United States Patent [19]
Sheffer et al.

[11] Patent Number: 6,066,138
[45] Date of Patent: May 23, 2000

[54] MEDICAL INSTRUMENT AND METHOD OF UTILIZING SAME FOR EYE CAPSULOTOMY

[76] Inventors: Yehiel Sheffer, 10 Haazmaut Street, 30900 Zichron Yaakov; Itzchak Beiran, 29 Margalit Street, 34464 Haifa, both of Israel

[21] Appl. No.: 09/084,373

[22] Filed: May 27, 1998

[51] Int. Cl.$^7$ ................................................. A61B 17/36
[52] U.S. Cl. ........................... 606/49; 606/50; 606/29; 606/107
[58] Field of Search ................... 606/41, 42, 45–52, 606/107, 27–31

[56] References Cited

U.S. PATENT DOCUMENTS

| | | | |
|---|---|---|---|
| 4,301,802 | 11/1981 | Poler | 606/48 |
| 4,307,720 | 12/1981 | Weber, Jr. | 606/49 |
| 4,476,862 | 10/1984 | Pao | 606/50 |
| 4,481,948 | 11/1984 | Sole | 606/45 |
| 5,445,637 | 8/1995 | Bretton | 606/41 |
| 5,578,040 | 11/1996 | Smith | 606/41 |
| 5,599,345 | 2/1997 | Edwards et al. | 606/41 |
| 5,755,716 | 5/1998 | Garito et al. | 606/41 |
| 5,766,171 | 6/1998 | Silvestrini | 606/49 |

*Primary Examiner*—Michael Peffley
*Attorney, Agent, or Firm*—Mark M. Friedman

[57] ABSTRACT

A medical instrument including (a) a handle; (b) a cautery for burning a lens capsule of an eye at the periphery of a portion of the capsule to be removed during surgery, the cautery including a retractable-extendible cautery portion being retractable into and extendible from the handle, so as to permit insertion of the cautery portion through a small incision formed in the eye when retracted and thereafter to correspond to a peripheral extent of the portion of the capsule to be removed when extended; (c) a mechanism for retracting and extending the cautery portion, the mechanism being engaged by the handle; and (d) an arrangement for connecting the cautery with an electrical apparatus for heating the cautery portion, whereby the peripheral extent of the capsule portion to be removed is searable by the cautery portion when extended and heated.

11 Claims, 2 Drawing Sheets

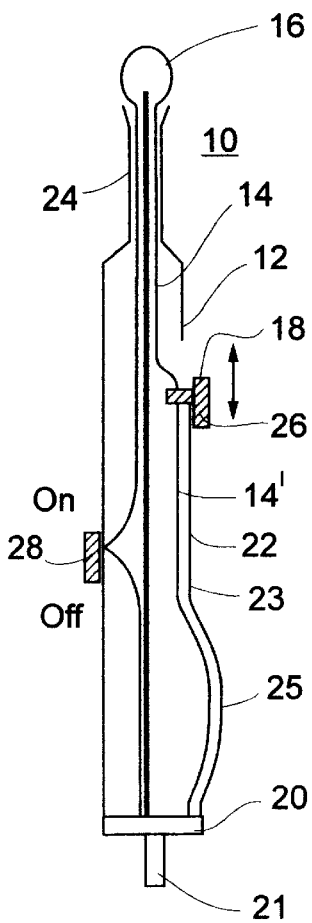
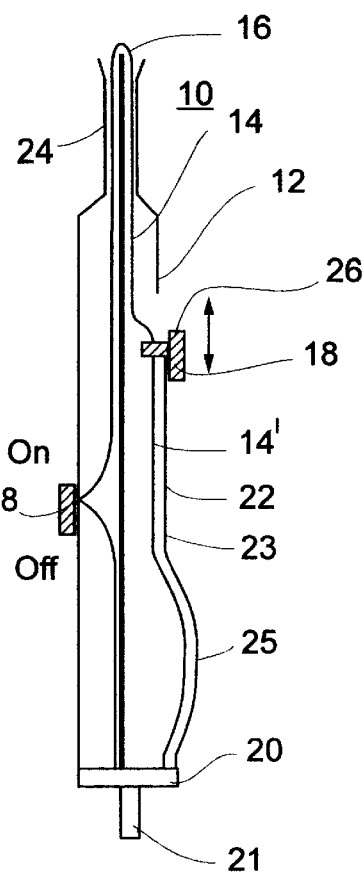
Fig. 1b   Fig. 1a
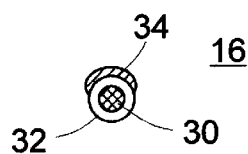
Fig. 3
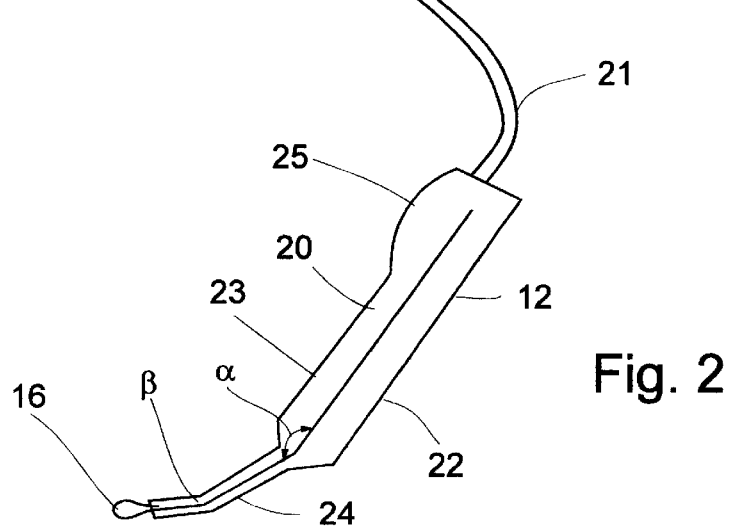
Fig. 2

MEDICAL INSTRUMENT AND METHOD OF UTILIZING SAME FOR EYE CAPSULOTOMY

FIELD AND BACKGROUND OF THE INVENTION

The present invention relates generally to a medical instrument for use in performing phacoemulsification or extracapsular cataract surgery, and a method for utilizing the medical instrument in performing such surgery. More particularly, the invention relates to a medical instrument for use in performing an anterior and/or posterior capsulotomy during phacoemulsification or extracapsular cataract surgery.

The medical instrument in accordance with the present invention includes a retractable-extendible wire cautery portion extendible to correspond to a desired peripheral extent of a portion of the capsule to be removed.

In performing a capsulotomy during cataract surgery by phacoemulsification, a small incision is made in the cornea through which the cautery portion is inserted while retracted to render it as small as possible. Thereafter, the cautery portion is extended and positioned in contact with the anterior (or posterior) lens capsule, so as to sear the periphery of a portion of the lens capsule to be removed. Thereafter, the entire periphery of the lens capsule portion to be removed is seared in a consistently perfect manner.

The human eye includes a lens having the configuration of a biconvex disc. The lens surface comprises a capsule which includes an anterior capsule and a posterior capsule which meet at an equator. Zonules extending from the ciliary body are attached to the lens equator so as to secure the lens in position. Disposed within the lens capsule is a softer cortex and a firm inner nucleus.

In a healthy human eye, the lens is formed of a clear crystalline protein, however, the lens will at times opacify to form what is known as a cataract.

Up to about five years ago, the preferred method employed to remove the cataract was the (manual) extracapsular technique. In such procedure, the eye is opened at the superior limbus, and either a bent needle (or any other curved sharp edged instrument) or special forceps are employed to open the anterior lens capsule and express from within the capsule the nucleus of the lens. Thereafter, the remaining cortical material is removed so as to thus leave a clear posterior lens capsule in the eye, which capsule provides a barrier between the anterior chamber and the vitreous cavity of the eye, as well as a resting surface for an implanted artificial lens.

In recent years phacoemulsification has become the procedure of choice for cataract extraction. In this procedure a small incision in either scleral or corneal region is made (with intracorneal portion—the "tunnel"). Through this incision an anterior opening in the lens capsule is performed. A probe containing an ultrasonic wave generator, a rinsing fluid inflow end and a suction tip is inserted into the capsular bag. Dense compacted proteins of lens nucleus are broken by ultrasonic power and are emulsified in rinsing fluid. Emulsified nuclear proteins as well as soft peripheral lens proteins ("cortex") are removed from the eye by the suction unit.

The main advantage of the phacoemulsification technique over the manual extracapsular technique is the small surgical wound needed to perform it. In manual extracapsular technique the nucleus of the lens is expressed from the eye as a whole. For this reason the surgical wound, in order to allow for the nucleus to be expressed, has to be about 7 millimeters wide.

As in phacoemulsification technique the nucleus is emulsified, it is no longer necessary for the surgical wound to be as wide, and 2–3 millimeters are sufficient.

A smaller wound is beneficial in regard to rate of visual rehabilitation after operation as well as post-surgical astigmatism prevalence and severity.

In performing cataract extraction by phacoemulsification two mandatory demands have to be met. First, surgical tools used for intraocular manipulations during surgery should be small enough in order to account for their insertion through the small surgical wound (2–3 millimeters in biggest dimension). Second, edges of the capsulotomy should be smooth and uniform. In contrast to extracapsular manual technique, in which non-homogenous edges of the capsulotomy were acceptable and allowed for different non-continuous capsular opening techniques (capsular puncture of interrupted cutting, later connected radially), in phacoemulsification non-uniform edges of capsulatory are unacceptable. The reason for this demand is that during phacoemulsification process the presence of an anterior capsular strands may result in capsular tear extending into the posterior capsule due to strands being captured and pulled by the suction unit. A tear in the posterior capsule prevents the posterior lens implantation in most cases and might result in vitreous loss.

At present opening of the anterior capsule during phacoemulsification is made by capsulophexis, whereby the surgeon opens a centrifugal linear opening in the capsule and then grips the anterior capsule edge with special forceps and creates a continuous circular tear of the anterior capsule.

Correctly performed, this maneuver results in a uniform smooth edge capsular opening yet expressing this technique demands high degree of surgical skill and if the surgeon loses dull control on tearing procedure, the tear might be directed posteriority and cause opening in posterior capsule with all its above mentioned complications.

Performance of a posterior capsulotomy wherein the posterior capsule remaining in the eye is itself incised is selective, depending upon the particular surgeon's preference. Such a technique may be employed to avoid the possibility of later opacification of the posterior capsule by performing the posterior capsulotomy in the final stages of the cataract extraction procedure, such as after an intraocular lens has been implanted.

Accordingly, and in view of the ever-increasing incidence of cataracts, there has developed a desideratum for a surgical instrument and technique for performing an anterior (or posterior) capsulotomy during phacoemulsification or extracapsular cataract surgery which overcomes the shortcomings and risks encountered using current instruments and techniques.

Some of the various attempts which have been made in the general field of cautery-type or heated-type medical instruments include: the "DENTAL INSTRUMENT" disclosed in U.S. Pat. No. 1,335,987 issued in 1920 to Reid et al; the "THERAPEUTIC APPLIANCE" disclosed in U.S. Pat. No. 1,615,828 issued in 1927 to Chesney; the "MEANS FOR EFFECTING THE BLOODLESS REMOVAL OF DISEASED TISSUE" disclosed in U.S. Pat. No. 1,919,543 issued in 1933 to Doane; the "METHOD OF AND APPARATUS FOR THE INTRACAPSULAR EXTRACTION OF THE CRYSTALLINE LENS OF AN EYE" disclosed in U.S. Pat. No. 2,033,397 issued in 1936 to Richman; the APPARATUS FOR INTRAOCULAR SURGERY" disclosed in U.S. Pat. No. 3,884,237 issued in 1975 to O'Malley et al; the "CAUTERY DEVICE FOR OPHTHALMIC OR THE LIKE SURGICAL APPLICATION" disclosed in U.S. Pat. No. 4,108,181 issued in 1978 to Saliaris; the "DEVICE FOR REMOVING EXCRESCENCES AND POLYPS" disclosed in U.S. Pat. No. 4,202,338 issued in 1980 to Bitrolf; the "EXPERIMENTAL INTRAOCULAR COAGULATION" disclosed in article by Peyman et al appearing in Opthalmic Surgery, January-February 1972, Volume 3, No. 1, pp. 32–37; and the "BIOPSY IN PROCTOLOGY" disclosed in an article by Gorsch appearing in American Journal of Surgery, June 1936, p. 484.

However, none of such known medical instruments and/or techniques provide any means for performing a consistently perfect capsulotomy during extracapsular cataract surgery.

U.S. Pat. No. 4,481,948 to Sole, entitled "MEDICAL INSTRUMENT, AND METHODS OF CONSTRUCTING AND UTILIZING SAME", which is incorporated by reference as if fully set forth herein, discloses a medical instrument including a cautery portion for use in performing an anterior or posterior capsulotomy during extracapsular cataract extraction surgery. A substantially rigid stem portion is connected between the cautery portion and a handle portion, and is provided with bends to facilitate maneuverability of the cautery portion and to avoid substantial interference with the surgical field of vision by the handle portion. An electrical path is defined through the handle portion and stem portion to the cautery portion so as to permit electrical current to be supplied to the cautery portion from an electrical apparatus which generates a radio frequency current. The cautery portion, as supplied with radio frequency current, becomes heated when in contact with an eye lens capsule so as to instantaneously and uniformly sear a peripheral extent of a portion of the lens capsule to be removed during surgery.

However, the medical instrument invented by Sole suffers limitations. First, having a wire cautery portion of a permanent size, it requires a large incision to be performed in the superior limbus in order to insert the wire in close proximity with the capsule, which incision should be wider than the diameter of the cautery portion employed, i.e., in the range of 7–10 millimeters. Second, although only one face of the cautery portion is effectively used to sear the periphery of a portion of an anterior (and/or posterior) capsule to be removed, the other face thereof heats as well, which may cause damage to neighboring eye tissue, such as the internal face of the cornea. Third, the cautery wire is rigid and is set at a constant diameter—a fact that does not allow for intraoperative diameter adjustment in accordance with relevant surgical factors like lens dimensions, puppilary dilation, etc.

There is thus a widely recognized need for, and it would be highly advantageous to have, a medical instrument devoid of the above limitation.

These limitations are avoided by the medical instrument of the present invention by providing a retractable-extendible cautery portion designed to have only one face thereof heated.

SUMMARY OF THE INVENTION

According to one aspect of the present invention there is provided a medical instrument comprising (a) a handle; (b) a cautery for burning a lens capsule of an eye at the periphery of a portion of the capsule to be removed during surgery, the cautery including a retractable-extendible cautery portion being retractable into and extendible from the handle, so as to permit insertion of the cautery portion through a small incision formed in the eye (e.g., at the cornea or sclera) when retracted and thereafter to correspond to a peripheral extent of the portion of the capsule to be removed when extended; (c) a mechanism for retracting and extending the cautery portion, the mechanism being engaged by the handle; and (d) an arrangement for connecting the cautery with an electrical apparatus for heating the cautery portion, whereby the peripheral extent of the capsule portion to be removed is searable by the cautery portion when extended and heated.

According to further features in preferred embodiments of the invention described below, the handle includes a main portion and a stem portion connected thereto and forms at least one obtuse angular bend in the handle, whereas the cautery portion is engaged by the stem portion.

According to still further features in the described preferred embodiments the cautery portion has a substantially circular shape when extended.

According to still further features in the described preferred embodiments the cautery portion has a substantially oval shape when extended.

According to still further features in the described preferred embodiments the stem portion is of about 2.5 millimeters in width.

According to still further features in the described preferred embodiments the mechanism includes a lever connected to the cautery or to an extension thereof, the lever is translatably engaged by the handle, such that translating the lever affects a degree to which the retractable-extendible cautery portion is retracted or extended.

According to still further features in the described preferred embodiments the medical instrument further comprising an on/off control button for controlling the heating of the cautery portion.

According to still further features in the described preferred embodiments the cautery portion includes a flexible wire covered with a flexible dielectric cover, the dielectric cover is heat-transmittive.

According to still further features in the described preferred embodiments the cautery portion further includes a flexible heat-insulative cover on one face thereof.

In another aspect of the present invention, there is provided a method for utilizing a medical instrument in performing phacoemulsification or extracapsular cataract surgery, comprising the steps of; (a) introducing a retracted cautery portion of the medical instrument into the eye; (b) extending the retracted cautery portion for obtaining an extended cautery portion; (c) positioning the extended cautery portion in contact with a surface of an anterior or posterior lens capsule of the eye; and (d) electrically heating the extended cautery portion so as to sear the lens capsule at a peripheral extent of a portion of the lens capsule to be removed during the cataract surgery.

According to still further features in the described preferred embodiments the method further comprising the step of (e) removing (e.g., pulling out) an anterior or posterior capsule of the eye (e.g., aided by forceps).

According to still further features in the described preferred embodiments the pupil of the eye to be operated is dilated.

It is an object of the present invention to provide a medical instrument including a retractable-extendible cautery portion which can be readily manipulated in size for minimizing the size of an incision required for its insertion into the eye, and which effects a clean, uniform searing of the lens capsule to ensure successful performance of a capsulotomy during phacoemulsification or extracapsular cataract surgery.

The above and other objects, details and advantages of the present invention will become apparent from the following detailed description, when read in conjunction with the accompanying drawings.

BRIEF DESCRIPTION OF THE DRAWINGS

The invention herein described, by way of example only, with reference to the accompanying drawings, wherein:

FIGS. 1a–b are longitudinal sections in of a medical instrument in accordance with the present invention;

FIG. 2 is a side view of a medical instrument in accordance with the present invention, shown connected to an electrical apparatus;

FIG. 3 is a cross sectional view through a cautery portion of the medical instrument in accordance with the present invention;

DESCRIPTION OF THE PREFERRED EMBODIMENTS

Figure 6:
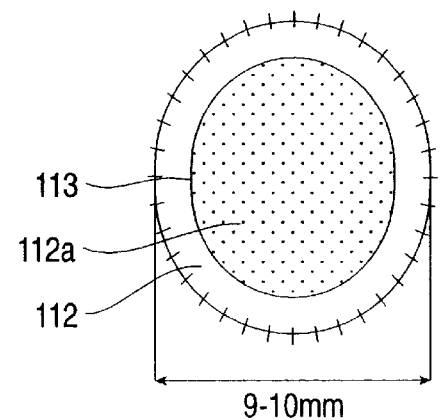
FIG. 6 is a top plan view of an anterior lens capsule showing a portion thereof to be removed during a capsulotomy.

The present invention is of a medical instrument for use in performing phacoemulsification or extracapsular cataract surgery, and a method for utilizing the medical instrument in performing such surgery. Specifically, the present invention can be used to perform an anterior and/or posterior capsulotomy during cataract surgery, and to enable searing of an entire periphery of a lens capsule portion to be removed in a consistently perfect manner.

The principles and operation of a medical instrument and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1a–b illustrate the medical instrument according to the present invention, which is referred to hereinbelow as medical instrument 10.

Thus, medical instrument 10 includes a handle 12, which is designed to be gripped by a surgeon. Handle 12 is substantially elongated and may have a generally cylindrical shape, or any other desired suitable shape. Handle 12 is preferably fabricated of an electrically-insulative material such as plastic or the like.

Medical instrument 10 further includes a cautery 14. Cautery 14 serves for burning a lens capsule of an eye at the periphery of a portion of the capsule to be removed during surgery. Cautery 14 includes a retractable-extendible cautery portion 16. Cautery portion 16 is retractable (as shown in FIG. 1a) into and extendible (as shown in FIG. 1b) from handle 12, so as to permit insertion of cautery portion 16 through a small incision (e.g., 2–3 millimeters wide) formed in the cornea or sclera of the eye when retracted, and thereafter to correspond to a peripheral extent of the portion of the capsule to be removed when extended.

Medical instrument 10 further includes a mechanism 18 designed for retracting and extending cautery portion 16. Mechanism 18 is engaged by handle 12. Mechanism 18 preferably includes a lever 26 connected to cautery 14 or to an extension thereof 14'. Lever 26 is translatably engaged by handle 12, such that translating lever 26 affects a degree to which retractable-extendible cautery portion 16 is retracted or extended. The overall diameter of cautery portion 16, when extended, is dependent upon the diameter of the pupil of the particular eye upon which surgery is to be performed. Therefore, cautery portion 16 is preferably allowed to extend to have diameters of about 9 millimeters, but may be acquired any smaller diameter as chosen by the surgeon according to the pupil diameter and other surgical considerations.

Medical instrument 10 further includes an arrangement 20 for connecting cautery 14 with an electrical apparatus for heating cautery portion 16, whereby the peripheral extent of the capsule portion to be removed is searable by cautery portion 16 when extended and heated.

Preferably, arrangement 20 is designed to electrically connect cautery 12 or an extension thereof with an electrical cord 21 to supply instrument 10 with electricity from an electrical apparatus. It should be noted that cautery portion 14 may be limited to cautery portion 16, whereas conductive elements 14' extending therefrom are used for (i) providing cautery portion 16 with electrical power, such that an electrically-conductive path is defined from cord 21, through handle 12 to cautery portion 16; and (ii) mechanically connecting cautery portion with mechanism 18, say lever 26. In any case, as further detailed below, instrument 10 is preferably powered and controlled by an electrical apparatus, which may receive power from the net or a battery. If miniaturized, the electrical apparatus may be housed within handle 12.

According to a preferred embodiment of the present invention, and as best seen in FIG. 2, handle 12 includes a main portion 22 and a stem portion 24 connected thereto and forms an obtuse angular bend α in handle 12, whereas cautery portion 14 is engaged by stem portion 24. Bend α is preferably of approximately 160°, for example, and is provided in order to minimize interference with the surgical field of vision, particularly by main portion 22 of handle 12, and to facilitate manipulation of cautery portion 16 when medical instrument 10 is being employed for use during surgery. Stem portion 24 is preferably about 2.5 millimeters in width (e.g., diameter), or less and about 55 millimeters in length. At least one additional bend β of about 160° is preferably provided in stem portion 24, for facilitating its insertion into the eye as further shown below. Main portion 22 is preferably about 120 millimeters in length and preferably includes a thinner middle part 23 of about 8 millimeters in diameter and a thicker end part 25 which serves both for improved gripping and for housing access of cautery 14 or an extension thereof 14' when retracted into handle 12.

According to another preferred embodiment cautery portion 16 has a substantially circular or substantially oval shape when extended.

According to a preferred embodiment of the invention medical instrument 10 further includes an on/off control button 28 which serves for controlling the heating of cautery portion 16.

FIG. 3 shows a cross section through cautery portion 16. Thus, cautery portion 16 includes a flexible wire 30 covered with a flexible dielectric cover 32. Dielectric cover 32 is selected heat-transmittive. Preferably, cautery portion 16 further includes a flexible heat-insulative cover 34 on one face thereof, such that only one face of cautery portion 16 heats when operated. Both covers 32 and 34 are selected heat-resistive, such that covers 32 and 34 withstands the temperatures developed by cautery portion 16. Suitable materials for covers 32 and 34 are ceramic materials.

Cautery portion 16 is selected as fine as possible while still being capable of reaching a suitable temperature for burning the anterior lens capsule of an eye in the presence of aqueous material, such temperature being in the order of, for example, about 500° C.

The entire instrument 10 may be provided in a disposable form.

A surgical technique utilizing medical instrument 10 as thus far described in performing cataract surgery, and particularly in performing a capsulotomy during cataract surgery, will now be described hereinbelow with reference to FIGS. 4–6.

Figure 4:
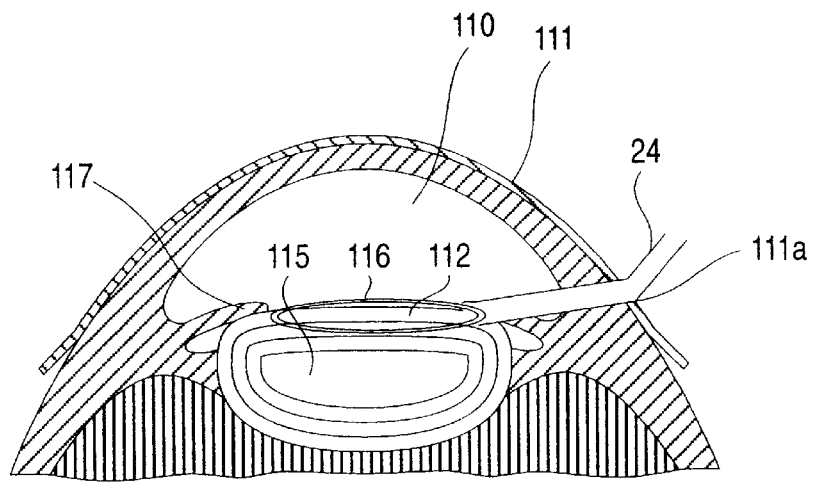
FIG. 4 is a sectioned side view of a human eye during a surgical procedure employing the medical instrument in accordance with the invention.
Figure 5:
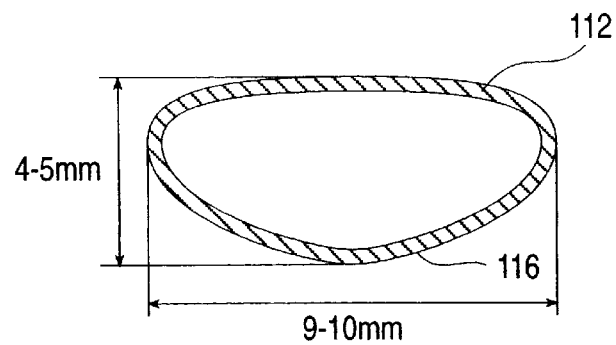
FIG. 5 is a sectioned side view of a lens of a human eye.

In FIG. 4, cautery portion 16 is shown in its extended form after being introduced into the anterior chamber 110 of the eye. To this end, a small incision (e.g., about 2–3 millimeters) is formed in cornea 111 or sclera 111a and cautery portion 16 is inserted therethrough when fully retracted. Thereafter, cautery portion 16 is extended to its desired size, e.g. to form a circular loop of about 6–9 millimeters, depending on the anatomy of the treated patient. The pupil of the eye is maximally dilated to permit positioning of cautery portion 16 in contact with the surface of the anterior lens capsule 112 without contacting other ocular structures. With cautery portion 16 thus positioned in contact with the surface of anterior lens capsule 112 as shown in FIG. 4, electrical current is applied to cautery portion 16. The very fine wire cautery portion 16 is rapidly heated by such applied current for an instant so as to burn a clean, substantially perfect and uniform circle 113 in the anterior capsule 112, as shown in FIG. 6. It will thus be understood that the medical instrument in accordance with the invention functions in a manner analogous to a conventional branding iron, although much more delicately, in burning circle 113 in anterior lens capsule 112. After circle 113 has been burned in anterior lens capsule 112 by means of cautery portion 16, the surgeon removes portion 112a (FIG. 6) of anterior lens capsule 112 within circle 113, e.g., by pulling it out. Thereafter, the cataract surgery is continued by phacoemulsification of the nucleus and aspiration of emulsified as well as soft cortical remnants, so as to leave only a clear posterior lens capsule 116 (FIG. 4) within the eye to serve as a barrier between the anterior chamber and the vitreous cavity. In case the surgeon chooses to perform a manual extracapsular surgery, capsulotomy is followed by nucleus expression and cortex aspiration by conventional techniques, however, the drawback of this procedure is the need for a larger incision.

The medical instrument as described hereinabove should be fabricated so as to be very light in overall construction, so as to avoid excessive posterior pressure on the lens during the anterior capsulotomy. Further, consideration should be given to the overall construction and the material forming the various component portions of the instrument to ensure that cautery portion 16 will reach its burning temperature as rapidly as possible, maintain such temperature only long enough to bum circle 113, and then cool. In this regard, it will be understood that any suitable switches and/or other electrical circuitry components may be employed to effect the aforesaid heating and cooling characteristics.

Because stem portion 24 is made of an electrically-insulative material (e.g., plastic), and because cautery portion includes a heat-insulative cover 34 (FIG. 3) covering one face thereof as described hereinabove, it will be understood that inadvertent burning of the iris 117, cornea 111 or sclera 111a (FIG. 4) will be effectively avoided.

As further shown in FIG. 2, medical instrument 10 is supplied with power from an electrical apparatus 40 to which cord 21 connects and which includes an on/off control button 41, a temperature control potentiometer 42 for controlling the temperature of cautery portion 16, a digital temperature display 44 for rough indication of the actual temperature of cautery portion 16, simple indicators such as light and sound indicators 46, for signaling when cautery portion 16 reaches a desired temperature.

One ordinarily skilled in the art would know how to devise apparatus 40 which functions as herein described.

Medical instrument 10 may be supplied with RF current or a conventional electrical current. If RF current supply is of choice, medical instrument 10 is supplied with power from an electrical apparatus which generates a radio frequency current supply, i.e., having frequency higher than 10,000 hertz. Such an apparatus might comprise, by way of example, an electrosurgical generator of a known type which is commonly employed in performing electrosurgical procedures in various fields of surgical specialty. One known electrosurgical generator suitable for use in supplying power to the medical instrument in accordance with the invention is manufactured by Davol Inc. of Cranston, R.I., and is capable of producing a Bovie-like fulguration surgical effect as well as having both monopolar and bipolar capabilities.

One of the primary advantages afforded by employing RF current resides in the fact that the cautery portion will become heated only when it is brought into contact with the peripheral extent of the portion of the lens capsule to be removed, to thus effect the desired searing action without being heated previous thereto. In this case, the cautery portion is devoid of electricity-insulative covers.

The peripheral extent of the desired portion of capsule to be removed is thus instantaneously and perfectly uniformly seared by the cautery portion, as supplied with radio frequency current to effect a Bovie-like searing effect.

The above-described searing action, effected by means of radio-frequency current supplied to the cautery portion, provides an instantaneous, accurate and effective searing of the periphery of the lens capsule portion to be removed. Desirably, the aforesaid electrical apparatus which generates the RF current is provided with a conveniently operated actuating member, such as a foot pedal, to be operated by the surgeon when the cautery portion has been properly positioned in contact with the anterior lens capsule.

It will also be understood that normally an electrical grounding device is employed (such as by being positioned under the patient) in conjunction with electrosurgical procedures involving radio frequency current.

Further, as mentioned previously, the cautery portion will become heated by the RF current supplied thereto only when it is in contact with the resistance offered by the anterior lens capsule tissue, thus avoiding any undesirable heating of the cautery portion prior to its proper positioning.

The medical instrument according to the present invention enjoys two advantages as compared with the prior art, as for example disclosed in U.S. Pat. No. 4,481,948 to Sole. First, having a retractable-extendible cautery portion the instrument according to the present invention requires a much smaller incision made in the cornea or sclera (e.g., about 2–3 millimeters as compared with about 7–10 millimeters for the prior art instrument). Second, the diameter of the cautery portion is size adjustable according to surgical needs and preferences. Finally, featuring a heat-insulative face, the cautery portion of the instrument according to the present invention is less likely to inflict heat damage upon neighboring eye tissue.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A medical instrument, comprising:
   (a) a handle;
   (b) a searing cautery for burning a lens capsule of an eye at the periphery of a portion of said capsule to be removed during surgery, said searing cautery including a retractable-extendible searing cautery portion being retractable into and extendible from said handle, so as to permit insertion of said searing cautery portion through a small incision formed in the eye when retracted and thereafter to correspond to a peripheral extent of said portion of said capsule to be removed when extended;
   (c) a mechanism for retracting and extending said searing cautery portion, said mechanism being engaged by said handle; and
   (d) an arrangement for connecting said searing cautery with an electrical apparatus for heating said searing cautery portion, whereby said peripheral extent of said capsule portion to be removed is searable by said searing cautery portion when extended and heated.

2. The medical instrument of claim 1, wherein said handle includes a main portion and a stem portion connected thereto and forms at least one obtuse angular bend in said handle, whereas said searing cautery portion is engaged by said stem portion.

3. The medical instrument of claim 2, wherein said stem portion is of about 2.5 millimeters in width.

4. The medical instrument of claim 1, wherein said searing cautery portion has a substantially circular shape when extended.

5. The medical instrument of claim 1, wherein said searing cautery portion has a substantially oval shape when extended.

6. The medical instrument of claim 1, wherein said mechanism includes a lever connected to said searing cautery or to an extension thereof, said lever is translatably engaged by said handle, such that translating said lever affects a degree to which said retractable-extendible searing cautery portion is retracted or extended.

7. The medical instrument of claim 1, further comprising an on/off control button for controlling said heating of said searing cautery portion.

8. The medical instrument of claim 1, wherein said searing cautery portion includes a flexible wire covered with a flexible dielectric cover, said dielectric cover is heat-transmittive.

9. The medical instrument of claim 8, wherein said searing cautery portion further includes a flexible heat-insulative cover on one face thereof.

10. A method for utilizing a medical instrument in performing phacoemulsification or extracapsular cataract surgery, comprising the steps of:
    (a) introducing a retracted searing cautery portion of the medical instrument into said eye;
    (b) extending said retracted searing cautery portion for obtaining an extended searing cautery portion;
    (c) positioning said extended cautery portion in contact with a surface of an anterior or posterior lens capsule of said eye; and
    (d) electrically heating said extended searing cautery portion so as to sear said lens capsule at a peripheral extent of a portion of said lens capsule to be removed during said cataract surgery.

11. The method of claim 10, further comprising the step of:
    (e) removing an anterior or posterior capsule of the eye.

* * * * *